United States Patent [19]
Nakanishi

[11] Patent Number: 5,080,659
[45] Date of Patent: Jan. 14, 1992

[54] TAMPON

[75] Inventor: Takashi Nakanishi, Utsunomiya, Japan

[73] Assignee: KAO Corporation, Tokyo, Japan

[21] Appl. No.: 575,612

[22] Filed: Aug. 31, 1990

[30] Foreign Application Priority Data

Sep. 20, 1989 [JP] Japan .................................. 1-244465

[51] Int. Cl.$^5$ ............................................. A61F 15/00
[52] U.S. Cl. ...................................... 604/904; 604/15; 604/18
[58] Field of Search ................... 604/393, 904, 15, 16, 604/17, 18

[56] References Cited

U.S. PATENT DOCUMENTS

| | | | |
|---|---|---|---|
| 2,832,342 | 4/1958 | Wingenroth | 604/16 |
| 3,347,234 | 10/1967 | Voss | 604/18 |
| 4,269,187 | 5/1981 | Sakurai et al. | 604/904 |
| 4,286,595 | 9/1981 | Ring | 604/18 |
| 4,291,696 | 9/1981 | Ring | 604/904 |
| 4,412,833 | 11/1983 | Wiegner et al. | 604/18 |
| 4,479,791 | 10/1984 | Sprague | 604/18 |
| 4,857,044 | 8/1989 | Lennon | 604/904 |

Primary Examiner—David J. Isabella
Assistant Examiner—Trinh Nguyen

[57] ABSTRACT

A tampon has an accommodation barrel and an absorbent material housed within the accommodation barrel. The accommodation barrel in this tampon includes a flexible cylindrical sheet portion and a rigid cylindrical portion connected to the flexible cylindrical sheet portion. A front end portion of the flexible cylindrical sheet portion is connected with one end of a take-out device having a length longer than the accommodation barrel for removal of the accommodation barrel while the absorbent material remains positioned as inserted into a vagina.

8 Claims, 4 Drawing Sheets

Fig. 1
Fig. 2
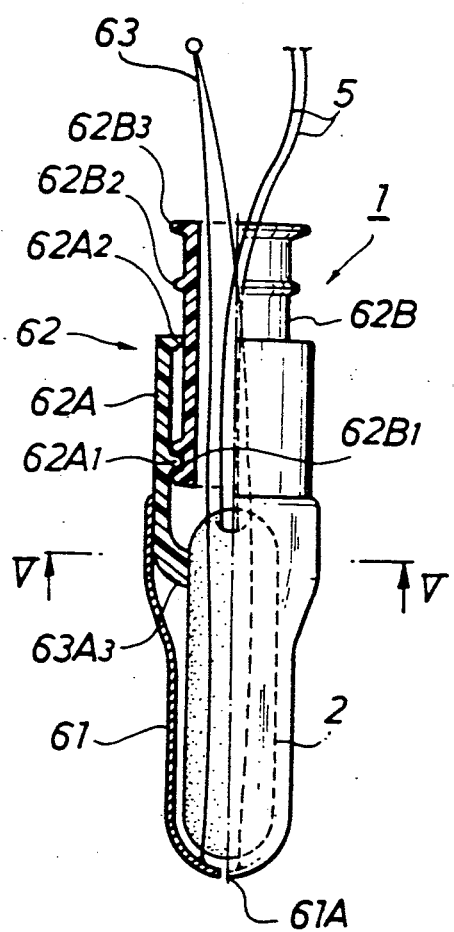
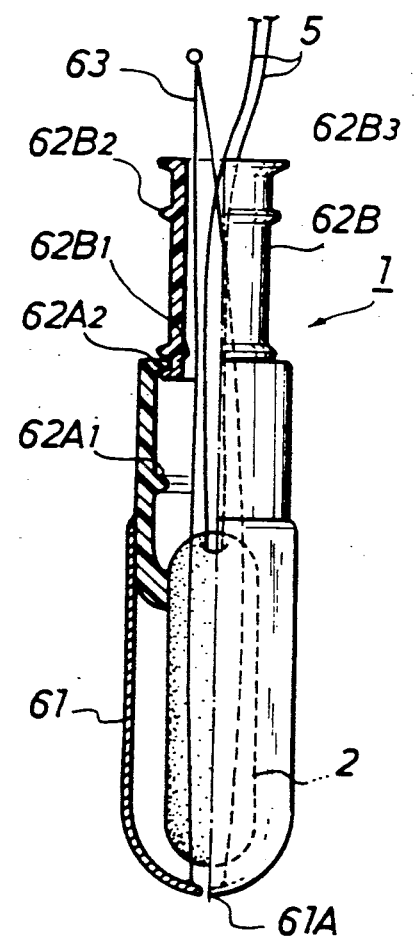

TAMPON

BACKGROUND OF THE INVENTION

1. Field of the Invention

This invention relates to a physiological good and more particularly to a physiological tampon having an absorbent material which can be easily vaginally inserted.

2. Description of Related Art

There are two types of tampons which are mostly used at present. One is an applicator type and the other is a finger type.

The applicator type tampon, as shown in FIG. 7, includes an outer barrel 3 for accommodating therein an absorbent material 2, and an inner barrel 4 which can be inserted into the outer barrel 3. The inner barrel 4 is provided with a tiny hole formed along its axis. This tiny hole serves as an aperture through which a pull string 5 is tensioned between the absorbent material 2 at the interior of the outer barrel 3 and end portion of an inner barrel 4. The absorbent material 2 used here is formed of an absorbent fiber compressed into a cylindrical shape.

Therefore, insertion of the applicator type tampon 1 is carried out in such a manner as shown in FIG. 8. That is, the base of outer barrel 3 is clamped with the thumb and the middle finger. Then, the index finger is abutted against an end face of the inner barrel. After the outer barrel 3 is inserted into and correctly positioned in a predetermined place of the body, preferably partially within the vagina, the inner barrel 4 is pushed in toward the outer barrel 4 with the index finger. Then, the absorbent material 2 accommodated in the outer barrel 3 is pushed out of the outer barrel 3 and inserted into a predetermined place of the body, preferably an upper portion of the vagina adjacent the cervix. Thereafter, the outer and inner barrels 3 and 4 are withdrawn from their partial insertions, thereby correctly setting the tampon in place.

On the other hand, the finger type tampon does not have an applicator. It merely comprises an absorbent material 2 and a pull-string 5 (see FIG. 9). When in use, the absorbent material 2 is directly set in place.

As the conventional tampon 1 of any of the above-mentioned types is difficult to set in place, such tampons 1 are not widespread among the general female population. It has heretofore been mentioned that, among them, a plastic applicator type tampon shown in FIG. 7 is comparatively effective for placement.

However, in the conventional applicator type tampon 1, a lump of cotton forming the absorbent material 2 is obliged to advance while being contacted with the wall of the vagina when the absorbent material 2 is pushed out of the applicator. Accordingly, frictional resistance between the absorbent material 2 and the wall of the vagina becomes great. In addition, it is difficult to fix the inserting direction when the tampon is inserted along the path of the vagina having a flat configuration in section. For these reasons, the conventional applicator type tampon 1 is difficult to use when inserting a tampon smoothly into a predetermined place.

SUMMARY OF THE INVENTION

An object of the present invention is to provide a tampon in which frictional resistance between an absorbent material and the wall of the vagina is removed so that the tampon can be smoothly inserted into a predetermined place in the vagina.

The present invention has achieved the above object by providing a tampon having an accommodation barrel and an absorbent material housed within the accommodation barrel, the accommodation barrel comprising a flexible cylindrical sheet portion and a rigid cylindrical portion connected to the flexible cylindrical sheet portion, a front end portion of the flexible cylindrical sheet portion being connected with one end of a take-out device having a length longer than the accommodation barrel.

According to a tampon of the present invention, by pulling out the take-out device after the accommodation barrel is inserted into the vagina, the front end of the flexible cylindrical sheet portion housing the absorbent material is pulled up so that it is peeled off the absorbent material and the work for setting the absorbent material in place can be finished without moving the absorbent material in the vagina.

Accordingly, in the tampon of the present invention, the absorbent can be set to a predetermined place within the vagina smoothly by removing the frictional resistance between the absorbent material and the vagina.

BRIEF DESCRIPTION OF THE DRAWINGS

FIG. 1 is a left-half sectional view showing one embodiment of a tampon of the present invention;

FIG. 2 is a sectional view corresponding to FIG. 1 showing a state immediately before the tampon of FIG. 1 is inserted;

DETAILED DESCRIPTION OF THE EMBODIMENT

Figure 3:
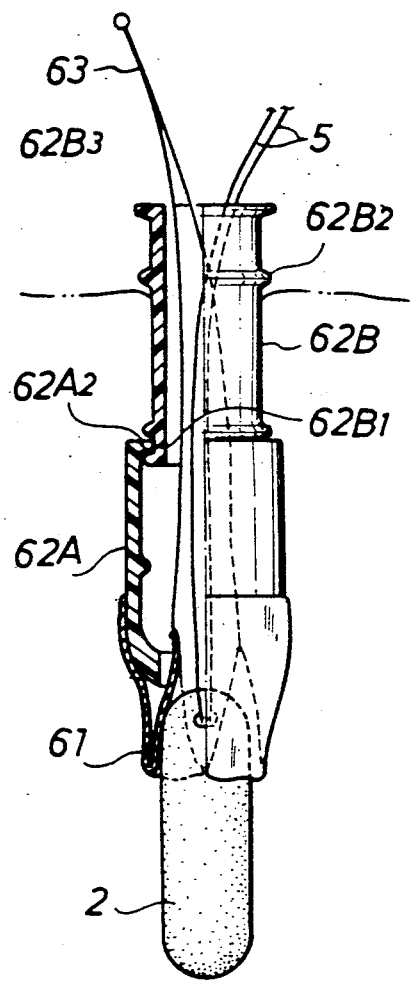
FIG. 3 is a sectional view corresponding to FIG. 1 showing a state after the tampon of FIG. 1 has been inserted into the vagina.
Figure 4:
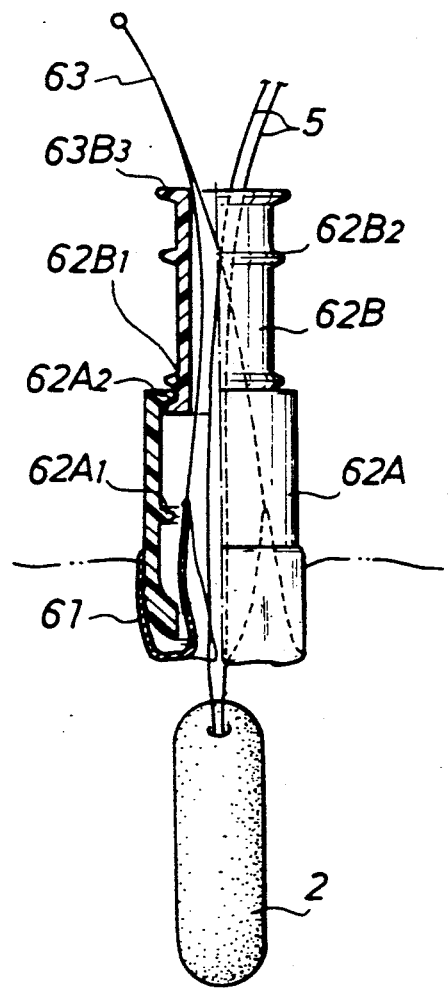
FIG. 4 is a sectional view corresponding to FIG. 1 showing a state where a flexible cylindrical sheet has been peeled off an absorbent material from the state shown in FIG. 3.

The features of the present invention will be described by way of one embodiment shown in FIGS. 1 through 6, in which identical or similar parts of the conventional tampon are represented by identical reference numerals.

An accommodation barrel 60 of a tampon 1 according to this embodiment, as shown in FIG. 1, is formed of a flexible cylindrical sheet portion 61 made of plastics and a rigid cylindrical portion 62 made of plastics with its front end engaged in one end of the flexible cylindrical sheet portion 61.

The flexible cylindrical sheet portion 61 has an absorbent material 2 housed therein, one end of the absorbent material 2 being engaged in an open portion formed in a front end of an outer barrel portion 62A of the rigid cylindrical portion 62. The flexible cylindrical sheet portion 61 is also provided with an opening 61A formed in a front end thereof, a peripheral edge of the opening 61A being provided with a plurality of broken lines formed of, for example, a plurality of perforations, so that the opening 61A can be easily ruptured when the flexible cylindrical sheet portion 61 is removed from the absorbent material 2. Also, by applying a lubrication oil to the outer peripheral surface of the flexible cylindrical sheet portion 61, the absorbent material 2 can be inserted with ease.

The opening 61A is also provided with a take-out device (take-out string in this embodiment) 63, one end of which is connected to the peripheral edge portion of the opening 61A and the other end of which is pulled outside via the interiors of the respective cylindrical portions 61 and 62.

On the other hand, the rigid cylindrical portion 62 comprises the outer barrel portion 62A and an inner barrel portion inserted into the outer barrel portion 62A, the outer barrel portion 62A being provided with a projection $62A_1$ formed in the circumferential direction of the inner peripheral surface in the vicinity of a front end of the outer barrel portion 62A, the inner barrel portion 62B being provided with a groove $62B_1$ formed between two projections in the circumferential direction of the outer peripheral surface of the front end of the inner barrel portion 62B, the inner barrel portion 62B being retained in the outer barrel portion 62A when the groove $62B_1$ and the projection $62A_1$ are engaged with each other, thereby to make the tampon 1 compact. Also, the inner barrel portion 62B is provided with a projection $62B_2$ formed in the circumferential direction of the outer peripheral surface in the vicinity of one end of the inner barrel portion 62B, a grip portion being formed between the projection $62B_2$ and a projection $62B_3$ formed on the outer periphery of one end thereof, so that it also serves as a stopper when the projection $62B_2$ is inserted. The outer barrel portion 62A is also provided with a projection $62A_2$ formed in the circumferential direction on an inner side of one end of the outer barrel portion 62A, so that it serves as a stopper for holding as an operating shaft when the tampon 1 is inserted in a state where the inner barrel portion 62B is pulled out from the outer barrel portion 62A because the projection $62A_2$ is brought into engagement with the groove $62B_1$ of the inner barrel portion 62B.

Figure 5:
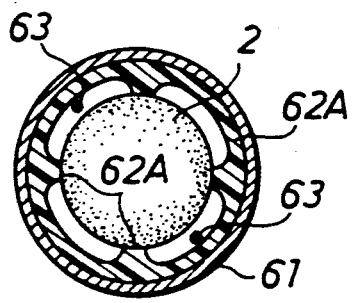
FIG. 5 is a sectional view taken on line V—V of FIG. 1.

The outer barrel portion 62A is provided with projections $63A_3$ formed at equal distances, as apparent from the sectional view taken in the lateral direction (taken on line V—V of FIG. 1) of FIG. 5, in the circumferential direction on the inner side of the opening formed at the front end of the outer barrel portion 62A, so that one end of the inserted absorbent material 2 is clamped by these projections $63A_3$. The take-out string 63 connected to the front end of the flexible cylindrical sheet portion 61 is pulled out from a gap between the projections $63A_3$ and $63A_3$ as mentioned above. The pull-out string 63, as shown in FIG. 2, is longer than the entire length of the tampon 1 when the groove $62B_1$ of the pulled-out inner barrel portion 62B is engaged with the projection $62A_2$ of the outer barrel portion 62A. Although a portion of the take-out string 63 pulled out from the inner barrel portion 62B is connected, it is preferable in view of operation if this portion is of a loop type.

The flexible sheet used for the flexible cylindrical sheet portion 61 may suffice if it has flexibility enough to be able to follow the movement of the pull-out string 63. As such flexible sheet material, there can be listed such synthetic resins as, for example, polytetrafluoroethylene, polyethylene, polypropylene, polyethylene terephthalate, and nylon. In case the flexible sheet is formed in a thickness of 60 μm with polytetrafluoroethylene, the flexible sheet has the following physical values.

① Tensile force of a film in the MD direction (longitudinal direction) is 1200 g/mm$_2$ and draw ratio thereof is 200%.

② Tensile force of a film in the TD direction (lateral direction) is 100 g/mm$_2$ and draw ratio thereof is 800%.

In case the flexible cylindrical sheet 61 is formed using the above-mentioned sheet, a portion which is not desired to be draw deformed is pressed and a portion which is desired to be draw deformed is left free, and in the foregoing state, the flexible cylindrical sheet portion 61 is drawn. As a result, the flexible cylindrical sheet portion 61 is drawn in one direction and contracted in the other direction, to thereby form an intended flexible cylindrical sheet portion.

On the other hand, the rigid cylindrical portion 62 may be formed of a material which is not substantially deformed at the time of insertion and which is able to transmit a pressing force to the absorbent material 2. As such materials, those formed of a synthetic resin as in the case of the flexible sheet are preferable. They may also be a sheet of paper having a sufficient strength.

Next, one mode for using the tampon 1 of this embodiment will be described.

First, the inner barrel portion 62B in the tampon 1 of this embodiment is pulled out of the outer barrel portion 62A, and the groove $62B_1$ of the inner barrel portion 62B is brought into engagement with the projection $62A_2$ of the outer barrel portion 62A and retained in a state where the inner barrel portion 62B is retracted (see FIG. 2). Then, the front end of the flexible cylindrical sheet portion 61 housing therein the absorbent material 2 is inserted into the vagina as far as the projection $62B_2$ of the inner barrel portion 62B, and then the tampon 1 is retained by the projection $62B_2$ of the inner barrel portion 62B. In the foregoing state, if the take-out string 63 is pulled, the flexible cylindrical sheet portion 61 is ruptured at the perforations formed in the opening 61A and retracted together with the take-out string 63 (see FIG. 3). Furthermore, if the take-out string 63 is retracted, the flexible cylindrical sheet portion 61 is completely peeled off the absorbent material 2 to allow the absorbent material 2 to be exposed in the vagina while remaining set in a predetermined place positioned by the projection $62B_2$ of the inner barrel portion 62B (see FIG. 4). Thereafter, when the inner barrel portion 62B is grasped and pulled out, the string 5 of the absorbent material 2 is pulled out of the accommodation barrel 6 and the absorbent material 2 remains in place connected to the absorbent material 2. That is, according to the tampon 1 of this embodiment, the positioning of the absorbent material 2 in the vagina is decided by the position where the applicator is inserted. Therefore, it is no longer required, as in the prior art, to move the absorbent material 2 furhter into the vagina after it is inserted therein. As a result, the direction of the absorbent material 2 is not charged in the vagina and when the applicator is inserted, the absorbent material 2 can be smoothly positioned in a desired place where it will reamain until extracted.

Figure 6:
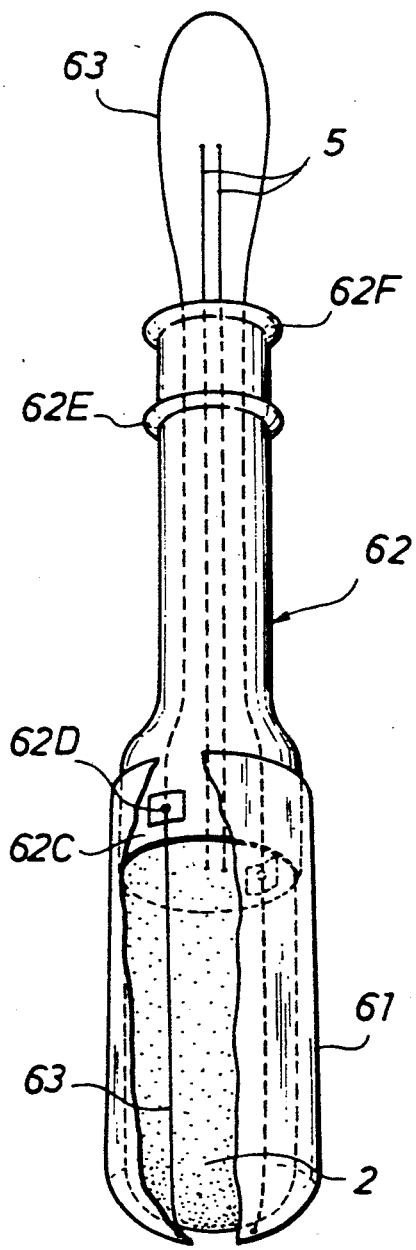
FIG. 6 is a perspective view showing a tampon according to another embodiment of the present invention, in which the flexible cylindrical sheet is partly broken.
Figure 7:
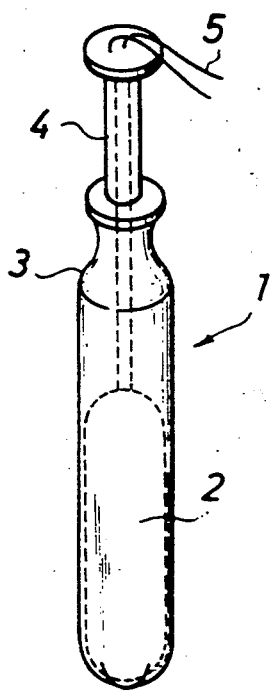
FIG. 7 is a perspective view showing a conventional applicator type tampon.
Figure 8:
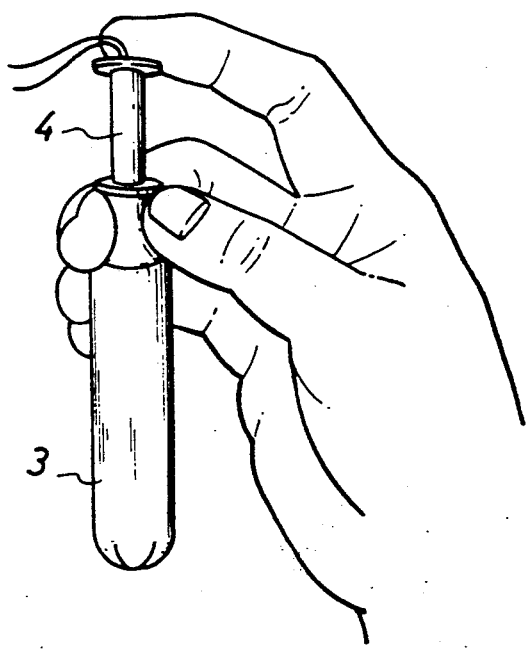
FIG. 8 is a perspective view showing a state where the tampon of FIG. 7 is being inserted.
Figure 9:
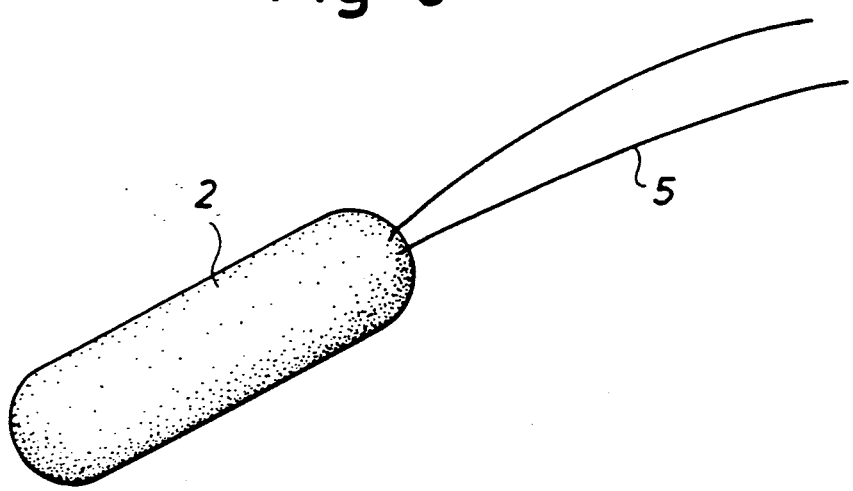
FIG. 9 is a perspective view showing a conventional finger type tampon.

FIG. 6 shows a tampon 1 according to another embodiment of the present invention. The tampon 1 of this embodiment, as shown in FIG. 6, is constructed in substantially the same manner as the tampon 1 of the previous embodiment, except that the rigid cylindrical portion 62 is of a different construction.

That is, although the rigid cylindrical portion 62 of the previous embodiment is of a two piece construction, the rigid cylindrical portion 62 of this embodiment is of a one piece construction and its front end portion is formed as a shaft member having a dilated cylindrical portion 62C, a part of the absorbent material 2 being engaged in the dilated cylindrical portion 62c and one end of the flexible cylindrical sheet portion 61 being mounted on the outer peripherial surface of the dilated cylindrical portion 62C. Furthermore, a pair of aperture 62D and 62d are formed in opposite positions of the dilated cylindrical portion 62C. Both ends of the folded take-out string 63 are pulled outside from the apertures 62D via of the interior of the shaft of the rigid cylindrical portion 62 with the folded portions thereof left outside, and connected to the front end of the flexible cylindrical sheet portion 61 through a space between the flexible cylindrical sheet portion 61 and the absorbent material 2. Also, on the outer peripheral surface of the shaft portion in the vicinity of one end of the rigid cylindrical portion 62, two annular ribbed projections 62E and 62F are disposed at a predetermined space so as to form a grip portion, the former projection 62E serving as a stopper when the tampon 1 is set in place. In the tampon 1 of this embodiment, there can be obtained the same function and effect as the tampon 1 of the above-mentioned embodiment. Furthermore,, since the tampon 1 according to this embodiment is designed such that once the take-out sting 63 is pulled out-side through the apertures 62D and 62d formed in the rigid cylindrical portion 62 and connected to the front end of the flexible cylindrical sheet portion 61, assembling of the absorbent material 2, etc. can be formed with ease.

In the above-mentioned embodiments, the take-out string (take-out device) 63 is connected to the front end of the flexible cylindrical sheet portion 61. However, in the present invention, it is sufficient for the take-out device to be connected to the front end portion of the flexible cylindrical sheet portion 61. The expression "front portion" used herein refers to a front end side with reference to the center in the longitudinal direction, and if the take-out device is connected to this portion, the flexible cylindrical sheet portion can be peeled off the absorbent material by the take-out device.

Also, in the above-mentioned embodiments, the take-out string 63 used as a take-out device pulled outside from one end of the accommodation barrel 60 via the inner side thereof. However, the tampon of the present invention may be disposed at an outer side of the accommodation barrel. In this case, since the flexible cylindrical sheet portion is pulled out along the wall of the vagina, the feeling of use is somewhat inferior but there can be expected the same function and effect as the above-mentioned embodiments. Also, even if the take-oiut device of the present invention is formed in other configurations than string-shape, the same function and effect can be expected.

What is claimed is:

1. A tampon comprising:
    a hollow accommodation barrel;
    an absorbent material disposed within said accommodation barrel, said accommodation barrel including a flexible cylindrical sheet portion and a rigid cylindrical portion connected to said flexible cylindrical sheet portion such that said absorbent material is primarily contained within said flexible cylindrical sheet portion; and
    a take-out device having a length longer than said accommodation barrel and connected to a front end portion of said flexible cylindrical sheet portion for removing said flexible cylindrical sheet portion from said absorbent material whereby after the accommodation barrel is inserted into the vagnia the front end of the flexible cylindrical sheet portion housing the absorbent material is pulled up within said rigid cylindrical portion so that the flexible sheet portion is peeled off the absorbent material and such that setting the absorbent material in place can be finished without moving the absorbent material in the vagina.

2. The tampon according to claim 1, wherein the rigid cylindrical portion comprises an outer barrel portion and an inner barrel portion inserted into the outer barrel portion, the outer barrel portion being provided with a projection formed in the circumferential direction of the inner peripheral surface in the vicinity of a front end of the outer barrel portion, the inner barrel portion being provided with a groove formed between two projections in the circumferential direction of the outer peripheral surface of the front end of the inner barrel portion, the groove and the projection being engaged with each other.

3. The tampon according to claim 1 or 2, wherein said take-out device is threaded through an interior of the flexible cylindrical sheet portion and the rigid cylidrical portion and includes a gripping end extermal of said rigid cylindrical portion.

4. The tampon according to claim 1, further including a pull-string connected to said absorbent material for applying a removal force to said absorbent material.

5. A tampon comprising:
    a hollow accommodation barrel;
    an absorbent material housed within said accommodated barrel; said accommodation barrel including a flexible cylindrical sheet portion and a rigid cylindricdal portion such that said absorbent material is primarily contained within said flexible cylindrical sheet portion; and
    wherein the rigid cylindrical portion includes an outer barrel portion and an inner barrel portion inserted into the outer barrel portion, the outer barrel portion being provided with a projection formed in the circumferential direction of an inner peripheral surface thereof in the vicinity of a front end of the outer barrel portion, the inner barrel portion being provided with a groove formed between two projections in the circumferential direction of an outer peripheral surface of the front end of the inner barrel portion, the groove and the projection being engaged with each other: a take-out device having a length longer than said accommodation barrel: whereby after the accommodation barrel is inserted into the vagnia the front end of the flexible cylindrical sheet portion housing the absorbent material is pulled within said rigid cylindrical portion so that the flexible sheet portion is peeled off the absorbent material and such that setting the absorbent material in place can be finished without moving the absorbent material in the vagina.

6. The tampon according to claim 5, wherein said take-out device is threaded through an interior of the flexible cylindrical sheet portion and the rigid cylindrical portion and includes a gripping end externally formed on said rigid cylindrical portion.

7. The tampon according to claim 5, wherein said take-out device is connected to a front end portion of said flexible cylindrical sheet portion for removing said flexible cylindrical sheet portion from said absorbent material without disrupting a position of said absorbent material.

8. The tampon according to claim 5, further including a pull-string connected to said absorbent material, for applying a removal force to said absorbent material.

* * * * *